United States Patent [19]

Creppy

[11] Patent Number: 5,496,856
[45] Date of Patent: Mar. 5, 1996

[54] ASPARTAME FOR ITS APPLICATION AS A THERAPEUTICALLY ACTIVE SUBSTANCE

[76] Inventor: Edmond Creppy, 16, Avenue Arago, 33600 Pessac, France

[21] Appl. No.: 332,768

[22] Filed: Nov. 1, 1994

[30] Foreign Application Priority Data

Dec. 16, 1993 [FR] France ................................... 93 15177

[51] Int. Cl.$^6$ .................................................. A01N 37/12
[52] U.S. Cl. ................................................................ 514/566
[58] Field of Search ............................................. 514/566

[56] References Cited

FOREIGN PATENT DOCUMENTS

| 1207232 | 8/1989 | Japan . |
| 2250917 | 6/1992 | United Kingdom . |
| 91/15197 | 10/1991 | WIPO . |

OTHER PUBLICATIONS

"Inhibition of Protein Synthesis in Mice by Ochtratoxin A and its Prevention by Phenylalanine", Food and Chemical Toxicology, vol. 22, No. 11, Mov. 1984, pp. 883–886.
Chemical Abstracts, Japan, 42621q, p. 449, Feb. 5, 1990, vol. 112, No. 6.
Chemical Abstracts, Japan, 150334q, p. 744, Apr. 13, 1992, vol. 116, No. 15.

*Primary Examiner*—Paul J. Killos
*Attorney, Agent, or Firm*—Dennison, Meserole, Pollack & Scheiner

[57] ABSTRACT

The present invention relates to aspartame for its application as a therapeutically active substance. It has been demonstrated that this compound has a protective action against human and animal ochratoxicosis which is capable of being applied in therapeutics.

15 Claims, No Drawings

ASPARTAME FOR ITS APPLICATION AS A THERAPEUTICALLY ACTIVE SUBSTANCE

The present invention relates essentially to aspartame for its application as a therapeutically active substance, and to pharmaceutical compositions in which it is present.

The invention is applicable especially in the treatment of certain diseases caused by contaminated foods, and more particularly in the treatment and prophylaxis of human and animal ochratoxicosis.

It is pointed out that aspartame is a synthetic dipeptide consisting of the methyl ester of L-aspartyl- L-phenylalanine of the formula

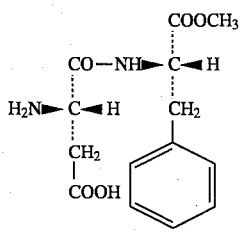

which is widely used in the food industry for sweetening a variety of products, on the one hand by virtue of its relatively intense sweetening potency (of the order of 100 to 200 times that of sucrose on a weight basis) and on the other hand by virtue of its low calorific value.

The preparation of aspartame is described in the patent U.S. Pat. No. 3,492,131, which is incorporated here by way of reference.

Because of its applications in the food industry, the toxicological properties of aspartame have been studied intensively.

However, no applications of this compound in the field of therapeutics have been described hitherto.

Now, it has been discovered, and it is this which constitutes the basis of the present invention, that aspartame has particularly valuable pharmacological properties and constitutes an excellent means for the treatment and prophylaxis of human and animal ochratoxicosis.

Ochratoxin A (also designated OTA hereafter) is a mycotoxin produced by *Penicillium verrucosum* and by numerous species of Aspergillus, in particular *Aspergillus ochraceus*. This mycotoxin has been shown to be present, sometimes in high proportions, in various cereals such as, for example, wheat, maize, barley, millet and rice, and in a variety of other foods such as, for example, beans, soya, peas, nuts, cocoa and coffee, as well as in meat products originating from poultry or pigs which have consumed contaminated foods, such as sausages.

Ochratoxin A exerts nephrotoxic effects on all animal species through the inhibition of protein synthesis and as a result of oxidative phenomena. This substance is generally considered to be responsible for endemic nephropathy in certain regions of the word (for example the Balkans) and for tumors of the urinary tract.

Various studies have shown that ochratoxin A is nephrotoxic in all animal species, as well as being genotoxic and carcinogenic in rodents and probably in man [E.E. Creppy et al., *Toxicol. Lett.* 28, 29–35 (1985); NPT (National Toxicology Program) Technical report on Toxicology and carcinogenesis studies of ochratoxin A, G. Boorman, Ed. NIH publication no. 89- 2813, USA; G. Dirheimer and E.E. Creppy, Mechanism of action of ochratoxin A in Mycotoxins, Endemic Nephropathy and Urinary Tract Tumours, Ed. M. Castegnaro, R. Plestina, G. Dirheimer, I.N. Chermozemski & H. Bartsch, Lyon, International Agency for Research on Cancer, Scientific Publication no. 115, pp. 171–185].

The chemical structure of ochratoxin A and its metabolites is known.

Thus ochratoxin A (or chlorodihydroisocoumarinylphenylalanine) has a chlorinated isocoumarin moiety linked to phenylalanine by a peptide bond.

This substance has general formula I below in which R is a hydrogen atom and R' is a chlorine atom.

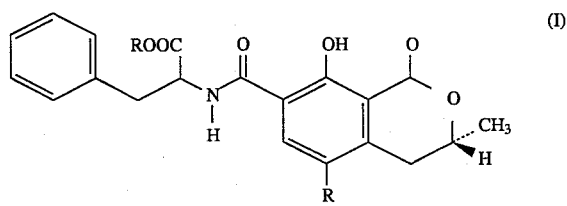

(I)

The corresponding non-chlorinated derivative (compound of formula I in which R and R' are a hydrogen atom) is called ochratoxin B. This substance does not seem to be toxic, although its genotoxicity has not yet been studied.

The ethyl ester of ochratoxin A (compound of formula I in which R is a $CH_3$ group and R' is a chlorine atom) is called ochratoxin C. This substance has effects comparable to those of ochratoxin A.

Likewise, the metabolism scheme of ochratoxin A below shows the different known metabolites of this substance.

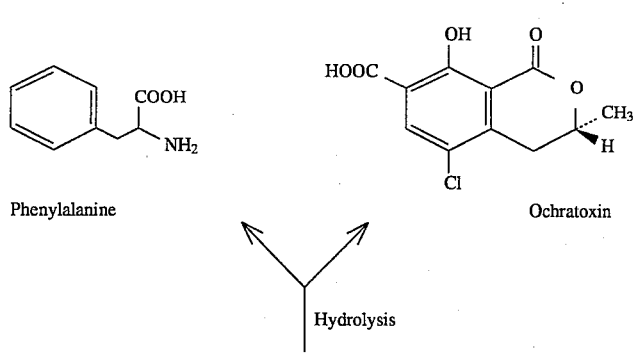
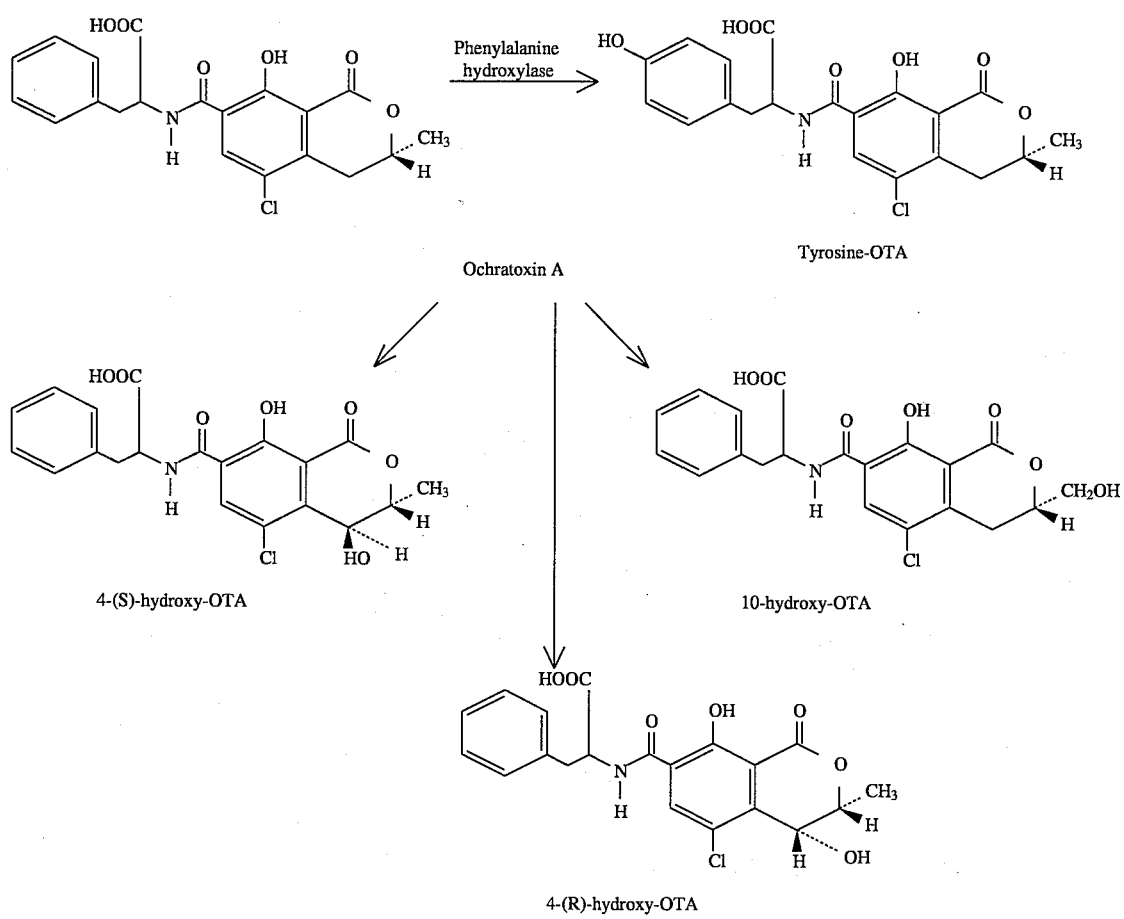

Because of the fact that it is extremely difficult to prevent the formation of mycotoxins, especially during the storage or transportation of foods susceptible to contamination, and even more particularly in the presence of heat and moisture, it has been found desirable to have access to therapeutic or prophylactic means of combating the effects of these mycotoxins, and in particular ochratoxin A.

Thus it has been proposed to use an alkali metal bicarbonate, and more particularly sodium bicarbonate, as the active principle of drugs intended for the treatment of ochratoxicosis [S. Yong et al., J, Environ. Sci. Health B22, 455–470 (1987)].

The efficacy of this treatment is still poor, however, even when the doses administered are relatively high, for example of the order of several grams per day.

Moreover, this treatment can lead to undesirable side-effects and cannot be applied to certain patients, for example patients on a sodium-free diet.

In addition, the administration of sodium bicarbonate causes acidification of the urine, which has the effect of increasing the lipophilic character of the ochratoxin A, as well as its distribution and possible accumulation in the tissues.

It has also been envisaged to use proteolytic enzymes, such as carboxypeptidase, in order to hydrolyze the ochratoxin A to ochratoxin a, which is non-toxic, and L-phenylalanine [L. Delacruz et al., J. Biopharm. Sci. 1 (3), 277–304 (1990)].

However, it has been shown that ochratoxin ct and L-phenylalanine recombine very rapidly in vivo to form ochratoxin A, thereby rendering this method ineffective.

Furthermore, because of its structural analogy with some of the metabolites of ochratoxin A, the use of phenylalanine has been envisaged for reducing the toxicity of this substance; however, the pharmacological results obtained are not totally satisfactory, especially as regards the chronic genotoxic and carcinogenic effects [E.E. Creppy et al., *Food Chem. Toxicol.* 22, 883–886 (1984); Dirheimer and Creppy, IARC Sc. Publication no. 115 (1991)].

Tyrosine-OTA, a metabolite resulting from the hydroxylation of OTA in the para-position of the benzene ring by phenylalanine hydroxylase, seems to be one of the metabolites responsible for the genotoxic effects, which apparently cannot be avoided by the use of phenylalanine [E.E. Creppy et at., *Arch. Toxicol.* 64, 279–284 (1990)].

Consequently, it will be borne in mind that although phenylalanine makes it possible to prevent the acute toxic effects and the inhibition of protein synthesis in vivo and in vitro, its action is very inadequate, if not non-existent, in cases of chronic intoxication.

The studies carded out by the inventor have made it possible to show that, totally surprisingly and unexpectedly, the administration of aspartame very substantially favors urinary elimination of the ochratoxin A present in the organism and constitutes an excellent means of prophylactic and therapeutic treatment in both man and animals.

It has also been observed that aspartame makes it possible on the one hand to prevent the binding of ochratoxin A to the plasma proteins, as well as its distribution and possible accumulation in the tissues, and on the other hand to slow down the metabolism and accelerate the elimination of ochratoxin A.

The experiments performed within the framework of the present invention have also made it possible to show that aspartame has a protective action against human and animal ochratoxicosis, especially by acting on the renal transporters to compete with ochratoxin, and by entering the renal cells preferentially, thus limiting the entry of ochratoxin into these cells and thereby favoring its elimination.

The results of the experiments performed also show that aspartame protects the kidney from the tubular and glomerular attacks caused by ochratoxin.

Finally, it has been found that aspartame opposes the toxic oxidative effects of ochratoxin A in vivo and in vitro and results in virtually complete disappearance of the DNA adducts.

Aspartame therefore prevents the most serious chronic effects (nephrotoxicity, genotoxicity and carcinogenicity). This beneficial effect can be extended to manifestations associated with subchronic exposure to ochratoxin A (teratogenicity, immunosuppression, etc.).

Consequently, aspartame can be used as a drug, for example in the form of various pharmaceutical preparations.

Thus the present invention covers pharmaceutical compositions intended especially for the treatment and prophylaxis of diseases resulting from foods contaminated by mycotoxins, and in particular human and animal ochratoxicosis, said compositions containing aspartame as the active principle, in association with a pharmaceutically acceptable carrier, vehicle or excipient.

These pharmaceutical compositions will generally be prepared by conventional processes and preferably administered orally, for example in the form of simple or coated tablets, gelatin capsules, granules or powder in sachets.

These compositions can contain the excipients normally employed in pharmaceutical compositions, such as, in particular, preservatives, solvents, stabilizers, wetting agents, emulsifiers, colors, flavorings, antioxidants and agents for controlling or sustaining the release of the active principle.

The posology will vary according to the complaint treated and the subject in question.

In human therapeutics, the daily dose which can be used is between 1 and 2000 mg of active principle (in one or more dosage units). The harmlessness of aspartame allows higher doses to be used.

In animal therapeutics, the daily dose which can be used is about 1 to 100 mg per kg.

Under these conditions, the pharmaceutical compositions according to the present invention will preferably take the form of unit doses which can contain from 1 to 2000 mg of aspartame.

Aspartame can also be used as a drug in the form of sweets, lozenges or gums containing up to 2000 mg of active principle in order to allow for possible losses in the buccal cavity.

Aspartame can also be used in its present form of pastilles to be dissolved in liquid and solid foods, the concentration being adapted so that the person can absorb the required amount per dosage unit or per day.

According to a third feature, the present patent application aims to cover the use of aspartame for the manufacture of a drug intended for the treatment and prophylaxis of diseases resulting from contaminated foods, and in particular human and animal ochratoxicosis.

According to a fourth feature, the present patent application aims to cover a method for the treatment and prophylaxis of human and animal diseases resulting from contaminated foods, comprising administering to the human or animal in need thereof, an effective amount of aspartame.

In particular, said human and animal disease is ochratoxicosis.

Other advantages of the present invention will become apparent from the following description of experiments which made it possible to establish the abovementioned pharmacological properties of aspartame.

The efficacy of aspartame in preventing the nephrotoxicity induced by ochratoxin, compared with known substances, was tested by determining the effects of the test substances on the excretion of creatinine, as well as renal enzymes and proteins. The toxin was administered under conditions comparable to those of natural contamination (on average 4 ppm per 48 h).

Distribution of the animals into cages

Male mice of the Swiss strain weighing 32±2 g are distributed into cages in groups of 5. The animals are classified in order of increasing weight and distributed randomly into 4 groups of 5 mice (homogeneous distribution by randomization).

Treatment with ochratoxin A

An amount of ochratoxin A corresponding to 289 µg/kg of body weight is given to the mice via an esophageal tube every 48 h for one week; the toxin is dissolved in 0.3 ml of 0.1M $NaHCO_3$, pH 7.4.

Controls 0.3 ml of 0.1 M $NaHCO_3$, pH 7.4, is given in the same way to the mice used as controls.

Treatment with aspartame 4 groups of 5 mice were studied.

Group I: control mice treated with 0.1 M $NaHCO_3$, pH 7.4

Group II: mice treated with ochratoxin A (289 µg/kg)

Group III: mice treated with ochratoxin A (289 µg/kg)+ aspartame (30 mg/kg)

Group IV: control mice treated with aspartame only.

The aspartame is administered in 0.3 ml of $H_2O$ one hour after the last administration of ochratoxin A.

Transfer to metabolic cages

The mice are placed in a metabolic cage for 15 hours and then sacrificed.

The creatinine is assayed in the 15-hour urine and serum.

The results of the urine and serum assays show that there is a rise in creatininemia and a simultaneous drop in creatininuria in the mice treated with ochratoxin A (difference relative to the controls significant at p=0.005).

The serum creatinine/urine creatinine ratio is two to three times higher in the treated mice than in the controls as a consequence of a deterioration in the glomerular filtration.

The aspartame treatment very markedly reduces the increase in serum creatinine observed in the mice treated with ochratoxin only, but increases the level of urine creatinine, which is similar to the control values.

The effects of aspartame on the level of serum creatinine and the serum creatinine/urine creatinine ratio, i.e. indirectly on the glomerular filtration, consequently appear to be beneficial.

The effects of aspartame on the elimination and detoxication of ochratoxin A are measured by the method indicated above, ochratoxin A being administered under conditions comparable to those of natural contamination, i.e. on average 4 ppm/48 h.

Distribution of the animals into cages

The animals used in this experiment are male rats of the Wistar strain weighing 160±10 g. The animals are classified in order of increasing weight and distributed randomly into 4 groups of 6 rats (homogeneous distribution by randomization).

Treatment with ochratoxin A

An amount of ochratoxin A corresponding to 289 μg/kg of body weight is given to the rats by gavage every 48 hours for 3 weeks; the toxin is dissolved in 0.3 ml of a 0.1 M solution of $NaHCO_3$, pH 7.4.

Controls

Some of the control rats did not undergo any treatment and the others were given 0.3 ml of 0.1 M $NaHCO_3$, pH 7.4.

Treatment with aspartame

The aspartame is administered by gavage, at the same time as the ochratoxin A, every 48 hours for 3 weeks.

The groups have the following constitution:

Group I: control rats (blanks)

Group II: control rats treated with 0.1 M $NaHCO_3$, pH 7.4

Group III: rats treated with ochratoxin A (289 μg/kg)

Group IV: rats treated with ochratoxin A (289 μg/kg)+ aspartame (25 mg/kg).

Transfer to metabolic cages

The control and treated rats are placed in a metabolic cage for 24 hours for urine sampling and then sacrificed.

The results of the serum and urine creatinine assays in the rats treated with ochratoxin A on the one hand, and with the ochratoxin A/aspartame combination on the other, show a significant reduction in the level of serum creatinine in the presence of aspartame and a parallel increase in the level of urine creatinine, which is comparable to the control level.

The results obtained show that aspartame protects against the renal attack induced by ochratoxin A by reducing the concentration of ochratoxin in the renal cells.

It is also known that the activity of certain enzymes (LAP, PAL, LDH, γ-GT), which is normally low in urine, increases in the urine of rats treated with ochratoxin A (A. Kane et al, Toxicology 42, 233–243 (1986)]. This increase is associated with a destruction of the tubular cells.

Now, it is found that the aspartame treatment as indicated above appreciably reduces the increase in the enzymic activities caused by ochratoxin A, the values recorded with the treated rats not being significantly different from those of the controls. This shows that aspartame exerts a protective effect against the tubular attacks induced by ochratoxin.

The results of the experiments also show that the aspartame treatment reduces the increase, induced by ochratoxin, in the level of urine proteins.

Finally, the serum and urine assays of ochratoxin show that the aspartame treatment significantly increases the urinary elimination of ochratoxin, which largely explains the prevention of nephropathy and confirms the value of aspartame in this indication.

The organs of the same animals were used for extraction of the DNA, which was analyzed by the technique of postlabeling with ATP gamma 32P in order to evaluate the genotoxicity by the presence of adducts with DNA bases.

Adducts are detected in large numbers in the organs (liver, kidney, spleen, etc.) of the animals treated with OTA, whereas the DNAs of the organs of the animals treated with aspartame and OTA are comparable to those of the controls. Aspartame therefore effectively opposes the genotoxic effects of OTA and hence its carcinogenicity.

Thus the results of the experiments performed have shown that the administration of aspartame according to the invention suppresses not only the nephrotoxic effects but also the genotoxic effects.

These results were confirmed by a series of experiments similar to those described hereinabove after administration of ochratoxin A (OTA) for six weeks instead of one week.

A further study was performed in order to determine the effect of aspartame on OTA binding on human plasma proteins in vitro.

MATERIAL AND METHODS

An in-vitro study was performed on plasma samples obtained from healthy human volunteers, from a French blood bank (Centre de transfusion sanguine in Bordeaux), using citrate as anticoagulant. Blood samples were centrifuged at 1800 g for 30 minutes. This pooled human plasma contained 41±3 g of proteins per liter.

Static diffusion cells (polypropylene, homemade according to the model provided by Nalgene, USA) containing two compartments (upper and lower) separated by a dialysing membrane having a 10 000 D exclusion limit (Sigma Chemical, USA) were used. This membrane allows OTA and aspartame diffusion and not protein diffusion.

A human plasma sample was placed in the upper compartment and a medium (RPMI 1640, Sigma chemical, USA) in the lower one.

The plasma binding properties of OTA were evaluated under two different conditions:

(i) The aspartame at a concentration of 10 μg/ml was added in the upper compartment containing human plasma proteins before introducing OTA at three different concentrations (20, 100, and 500 μg/ml) in the lower compartment;

(ii) The upper compartment contained human plasma proteins only and OTA (20, 100 and 500 μg/ml) was added into the lower compartment alone or concommitantly with 10 μg/ml aspartame.

OTA concentration in the upper compartment was determined by HPLC (Mobile phase: methanol, acetonitrile, acetic acid, sodium acetate 5 mM (300: 300: 400: 14 v/v/v/v); injection volume 50 μl; flow rate 1 ml/min; run time for one cycle: 10 min and fluorescence detection (excitation at 340 nm and emission at 465 nm).

Before extraction of OTA from the plasma, all the studied samples of plasma, which had already fixed OTA, were dialysed against free OTA RPMI medium for at least 15 minutes, one or several times, until no more OTA was found in the lower compartment.

The results obtained under condition (i) as defined hereinabove are reported in Table I, whereas the results obtained under condition (ii) are reported in Table II.

TABLE I

| OTA Concentrations (µg/ml) | Time (min) | Quantities of OTA bound to plasma proteins | |
|---|---|---|---|
| | | OTA alone (ng/ml) | OTA + Aspartame (ng/ml) |
| 20 | 30 | 215 ± 11 | 157 ± 12 |
| | 60 | 431 ± 18 | 97 ± 4 |
| | 120 | 772 ± 25 | 15 ± 3 |
| 100 | 30 | 442 ± 21 | 193 ± 17 |
| | 60 | 739 ± 17 | 74 ± 11 |
| | 120 | 1231 ± 17 | 55 ± 15 |
| 500 | 30 | 556 ± 15 | 275 ± 41 |
| | 60 | 1175 ± 71 | 296 ± 45 |
| | 120 | 1744 ± 112 | 345 ± 51 |

TABLE II

| OTA Concentrations (µg/ml) | Time (min) | Quantities of OTA bound to plasma proteins | |
|---|---|---|---|
| | | OTA alone (ng/ml) | OTA + Aspartame (ng/ml) |
| 20 | 30 | 163 ± 42 | 159 ± 13 |
| | 60 | 488 ± 41 | 53 ± 6 |
| | 120 | 774 ± 43 | 39 ± 4 |
| 100 | 30 | 491 ± 39 | 245 ± 15 |
| | 60 | 983 ± 48 | 459 ± 27 |
| | 120 | 1296 ± 61 | 587 ± 38 |
| 500 | 30 | 539 ± 41 | 516 ± 19 |
| | 60 | 1347 ± 92 | 1127 ± 89 |
| | 120 | 1899 ± 89 | 1789 ± 56 |

DISCUSSION

Table I shows that the efficiency of aspartame in preventing the binding of OTA on human plasma proteins is excellent (about 98 %) for OTA concentrations as high as 20 µg/ml. Only 2% of the OTA available is bound as compared to the control without aspartame. The concentration of 20 µg/ml corresponds to an intake of 20 mg/kg of food, which is considerably higher than that resulting from average natural contamination.

With OTA concentrations of 100 µg/ml only 4.5% of the OTA available is bound, whereas at 500 µg/ml 19.8% of the OTA available is bound to plasma proteins as compared to control without aspartame.

Thus the efficiency of aspartame in preventing the binding of OTA to plasma proteins is inversely proportional to the concentrations of OTA.

With 10 µg/ml of aspartame, i.e. 10 mg/l, there is practically no OTA bound.

This plasma concentration of aspartame can be obtained by the administration of 400 to 600 mg of aspartame within 24h, per os.

Under condition (ii) (Table II), the aspartame was put in the same compartment as OTA in the non-plasmatic compartment to mimic the stomach (the ration OTA/aspartame= 1.5 to 36).

In these conditions, it is not surprising that OTA binds first to the plasma proteins and then the aspartame removes it in time for OTA concentrations ranging from 20 to 100 µg/ml. It is noted that for an OTA concentration of 100 µg/ml, aspartame can only prevent 50% of the binding of OTA, whereas for an OTA concentration of 500 µg/ml aspartame is no longer efficient.

The efficiency of aspartame in preventing the binding of OTA on human plasma proteins is also very good when OTA is placed in the lower compartment to mimic stomac (more than 95%) for OTA concentrations as high as 20 µg/ml. The concentration of 20 µg/ml corresponds to a intake of 20 mg/kg of food, which is considerably higher than that resulting from average natural contamination.

The aspartame being more efficient in the plasma than in the stomach, it would be preferable to use it at least 1 or 2 hours before eating.

CONCLUSION

1—In normal conditions, with OTA concentrations lower than 20 µg/ml, the efficiency of aspartame in preventing the OTA binding on human plasma proteins is of at least 95%.

2—Aspartame could be in competition with OTA for binding on the site of high affinity, whereby it is fixed when the toxin concentrations are low.

3—Aspartame used in this way clearly exerts a preventive effect.

Several non-limiting Examples of pharmaceutical preparations incorporating aspartame as the active principle will now be given below.

EXAMPLE 1

Aspartame tablets

| 1. Aspartame | 100 mg |
|---|---|
| 2. Lactose | 200 mg |
| 3. Polyvinylpyrrolidone | 55 mg |
| 4. Talc | 15 mg |
| 5. Magnesium stearate | 30 mg |

Components 1, 2 and 3 are mixed dry in a planetary mixer. The mixture is then moistened with ethanol (90°). The moist mass obtained is granulated in a Frewitt granulator fitted with a sieve of mesh size 1.5 mm. The granules obtained are dried in an oven at 50° C. for 6 hours. 4 and 5 are then added. The whole is mixed carefully and then compressed to give a tablet containing 100 mg of aspartame and having a unit weight of 400 mg.

| Aspartame | 200 mg |
|---|---|
| Lactose | 100 mg |
| Aerosil | 10 mg |
| Magnesium stearate | 20 mg |

The different ingredients are mixed using granular aspartame.

The mixture obtained is then distributed into 330 mg gelatin capsules (size no. 1) containing 200 mg of aspartame.

| | |
|---|---|
| Aspartame | 500 mg |
| Roferose G ® | 500 mg |
| Aerosil | 20 mg |
| Magnesium stearate | 20 mg |

The above components are mixed in a Lodige mixer for 2 times 3 minutes. The mixture obtained is homogeneous and will be distributed into 1.040 g sachets.

The above contents can be flavored with different flavorings, such as orange, coffee, cocoa, etc., to make the preparation more pleasant.

What is claimed is:

1. A pharmaceutical composition which contains aspartame as the active principle, in association with a pharmaceutically acceptable carrier, vehicle or excipient.

2. A pharmaceutical composition intended for the treatment and prophylaxis of human and animal diseases resulting from contaminated foods, said composition containing aspartame as the active principle, in association with a pharmaceutically acceptable carrier, vehicle or excipient.

3. A pharmaceutical composition according to claim 2, wherein said disease is ochratoxicosis.

4. A pharmaceutical composition according to claim 2 which is formulated for oral administration.

5. A pharmaceutical composition according to claim 4 which takes the form of unit doses containing 1 to 2000 mg of aspartame.

6. A process for the preparation of a pharmaceutical composition intended for the treatment and prophylaxis of human and animal diseases resulting from contaminated foods, said process consisting in incorporating a pharmaceutically effective amount of aspartame into a pharmaceutically acceptable carrier, vehicle or excipient.

7. A method for the treatment and prophylaxis of human and animal diseases resulting from contaminated foods, comprising administering to the human or animal in need thereof, an effective amount of aspartame.

8. A method for the treatment and prophylaxis of human and animal ochratoxicosis comprising administering to the human or animal in need thereof, an effective amount of aspartame.

9. A method according to claim 7, wherein said effective amount is between 1 and 2,000 mg of active principle per 24 hours in human treatment.

10. A method according to claim 8, wherein said effective amount is between 1 and 2,000 mg of active principle per 24 hours in human treatment.

11. A method according to claim 7, wherein said effective amount is between 1 and 100 mg of active principle per 24 hours in animal treatment.

12. A method according to claim 8, wherein said effective amount is between 1 and 100 mg of active principle per 24 hours in animal treatment.

13. A method according to claim 7, wherein said administering takes place orally.

14. A method according to claim 8, wherein said administering takes place orally.

15. A method according to claim 13, wherein said administering takes place one or two hours before eating.

* * * * *